US012748090B2

(12) United States Patent
Das

(10) Patent No.: US 12,748,090 B2
(45) Date of Patent: Sep. 29, 2026

(54) MITIGATION OF FREE CHLORINE INTERFERENCE FOR OZONE DETECTION USING AN INDIGO-BASED INDICATOR

(71) Applicant: Hach Company, Loveland, CO (US)

(72) Inventor: Amit Das, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 521 days.

(21) Appl. No.: 18/342,216

(22) Filed: Jun. 27, 2023

(65) Prior Publication Data

US 2025/0003936 A1 Jan. 2, 2025

(51) Int. Cl.

| | |
|---|---|
| ***G01N 33/00*** | (2006.01) |
| ***G01N 33/14*** | (2006.01) |
| *G01N 21/64* | (2006.01) |
| *G01N 21/77* | (2006.01) |
| *G01N 31/22* | (2006.01) |

(52) U.S. Cl.

CPC ......... *G01N 33/0039* (2013.01); *G01N 33/14* (2013.01); *G01N 21/643* (2013.01); *G01N 21/77* (2013.01); *G01N 31/223* (2013.01)

(58) Field of Classification Search

CPC ...... G01N 21/64; G01N 21/643; G01N 21/03; G01N 21/77; G01N 21/80; G01N 31/16; G01N 31/223; G01N 2021/6443; G01N 2021/7786; G01N 2021/6439; G01N 33/0039; G01N 33/02; G01N 33/14; G01N 33/18; Y10T 436/145555; Y10T 436/18; Y10T 436/20; Y10T 436/206664; Y10T 436/19; Y10T 436/193333

USPC ......... 436/96, 119, 124, 125, 127, 135, 163, 436/164, 172; 422/75, 82.08

See application file for complete search history.

(56) References Cited

U.S. PATENT DOCUMENTS

| | | | | |
|---|---|---|---|---|
| 5,116,759 A * | 5/1992 | Klainer | G01N 21/253 | 436/119 |
| 5,888,758 A * | 3/1999 | Wu | G01N 33/84 | 436/124 |
| 2003/0070996 A1* | 4/2003 | Hulsey | C02F 9/00 | 210/760 |
| 2012/0298529 A1 | 11/2012 | Malkov et al. | | |
| 2020/0064325 A1* | 2/2020 | Löbbert | G01N 27/40 | |

(Continued)

FOREIGN PATENT DOCUMENTS

| | | |
|---|---|---|
| CN | 111751304 A | * 10/2020 |
| JP | 08-304333 | * 11/1996 |
| WO | 2012/016350 A1 | * 2/2012 |

OTHER PUBLICATIONS

European Patent Office, International Search Report and Written Opinion, Sep. 19, 2024, 18 pages, EPO.

(Continued)

*Primary Examiner* — Maureen Wallenhorst

(74) *Attorney, Agent, or Firm* — Ference & Associates LLC

(57) ABSTRACT

An embodiment provides a method for measuring ozone in a sample, including: introducing an indigo-based indicator to a sample, wherein the sample contains an amount of ozone and the introducing causes a change in fluorescence intensity of the solution; introducing an ammonium salt to the sample; and measuring the amount of ozone in the sample by measuring the change in intensity of the fluorescence.

20 Claims, 6 Drawing Sheets

(56) References Cited

U.S. PATENT DOCUMENTS

| | | | | |
|---|---|---|---|---|
| 2020/0386682 | A1* | 12/2020 | Das | G01N 31/22 |
| 2023/0375514 | A1* | 11/2023 | Greenawalt | G01N 33/18 |
| 2024/0175817 | A1 | 5/2024 | Das | |

OTHER PUBLICATIONS

Koji Takeuchi et al., "Quantitative Determination of Aqueous-Phase Ozone by Chemiluminescence Using Indigo-5,5'—disulfonate", Analytical Chemistry, American Chemical Society, Mar. 15, 1989, 5 pages, vol. 61, No. 6, Analytical Chemistry, Washington, DC, United States.

* cited by examiner

MITIGATION OF FREE CHLORINE INTERFERENCE FOR OZONE DETECTION USING AN INDIGO-BASED INDICATOR

BACKGROUND

This application relates generally to measuring ozone in aqueous or liquid samples, and, more particularly, to the measurement of ozone using an indigo-based indicator.

Ensuring water quality is critical in a number of industries such as pharmaceuticals and other manufacturing fields. Additionally, ensuring water quality is critical to the health and well-being of humans, animals, and plants which are reliant on the water for survival. One element that is typically measured is ozone. Ozone may be controlled to make water safe for humans, animals, and aquatic life. Therefore, detecting the presence and concentration of ozone in water, food materials, or other liquid solutions is vital.

BRIEF SUMMARY

In summary, one embodiment provides a method for measuring ozone in a sample, comprising: introducing an indigo-based indicator to a sample, wherein the sample contains an amount of ozone and the introducing causes a change in fluorescence intensity of the solution; introducing an ammonium salt to the sample; and measuring the amount of ozone in the sample by measuring the change in intensity of the fluorescence.

Another embodiment provides a method for measuring ozone in a sample, comprising: introducing an indigo-based indicator to a sample, wherein the sample contains an amount of ozone and the introducing causes a change in fluorescence intensity of the solution; introducing an ammonium salt to the sample; adjusting the sample to a pH value; and measuring the amount of ozone in the sample by measuring the change in intensity of the fluorescence.

A further embodiment provides a measurement device which measures ozone in a sample, comprising: an indigo-based indicator; at least one measurement chamber; a processor; and a memory storing instructions executable by the processor to: introduce the indigo carmine indicator to a sample, wherein the sample contains an amount of ozone; introduce an ammonium salt to the sample; and measure the amount of ozone in the sample by measuring a change in fluorescence intensity of the sample.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
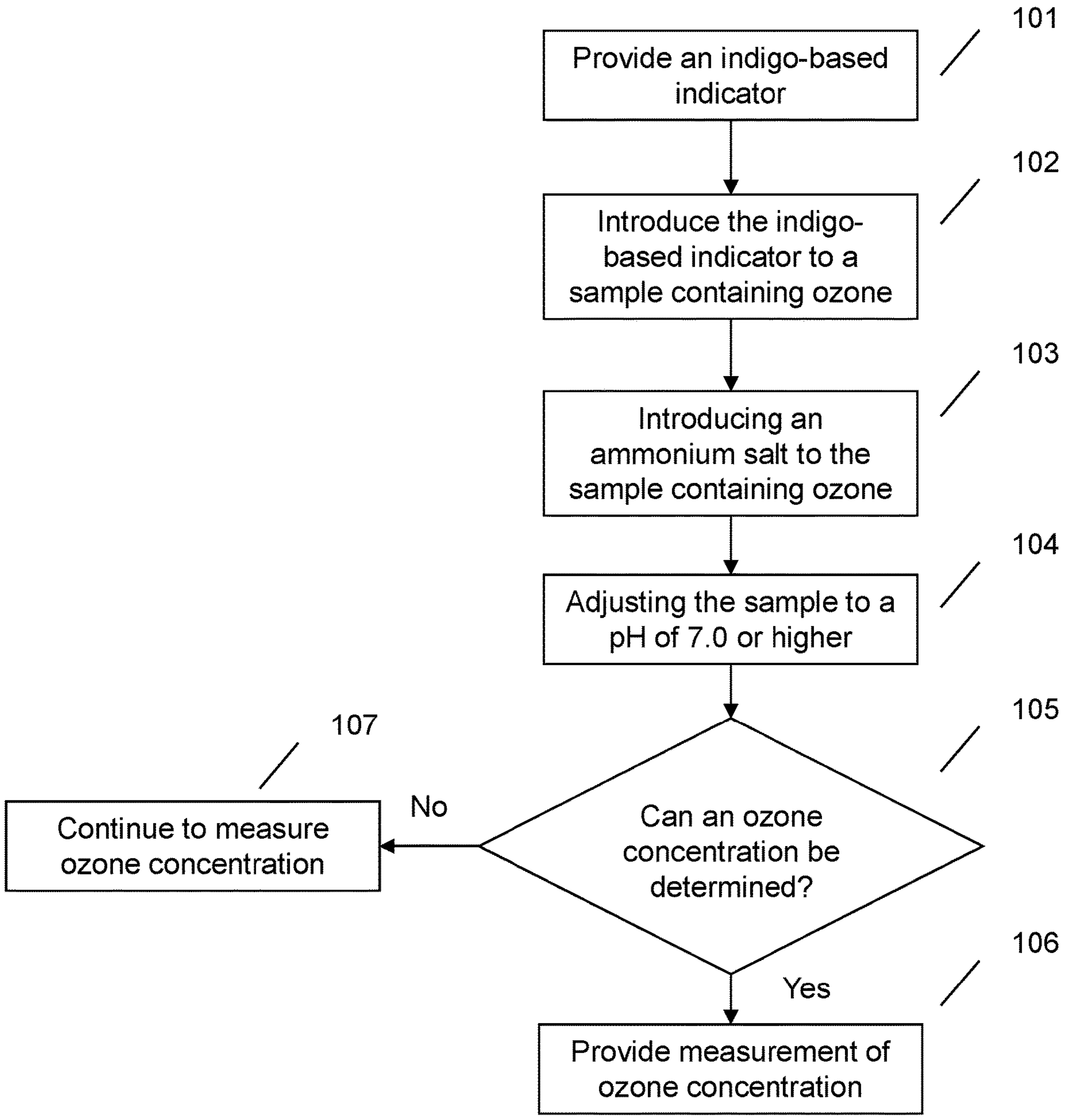
FIG. 1 illustrates a flow diagram of an example ozone measuring system for a sample.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Conventional methods of ozone measurement in water may have some limitations. For example, ozone measurement may be used to determine the quality of water. High concentrations of ozone may be harmful to animals, humans, and/or plants. Accordingly, as another example, a user or entity may want the ozone in a body of water to be under a particular threshold, therefore, the user may measure the ozone to determine if the amount of ozone is under that threshold.

A method of ozone measurement in water is Hach's AccuVac available from Hach Company, Loveland CO, USA (AccuVac is a registered trademark of Hach Company in the United States and other countries) which is a bleaching chemistry. These methods result in a bleaching of color in an amount proportional to the ozone concentration. The resulting color from the colorimetric reaction may be determined photometrically, for example, using a spectrophotometer. The amount of ozone may be determined by comparison to a similarly prepared blank vial with ozone free water. The absorbance of the sample reacted vial must be compared to the absorbance of the unreacted blank vial to determine the ozone concentration of the sample reacted vial.

The AccuVac ozone measurement system attempts to mitigate free chlorine interference. The mitigation uses a malonate buffer at a pH of 2.5. Other protocols may mitigate free chlorine using arsenite. The arsenite presents environmental issues. In other words, reaction solutions may have to be collected and disposed of properly. Further protocols for free chlorine mitigation may use reducing agents such as sulfite, bisulfite, dithionite, or the like.

However, the current analyte testing methods have limitations which are overcome by the methods and techniques as described in more detail herein. One limitation of the current techniques is that they use a bleaching chemistry not favorable to some users and measurement systems. Additionally, the traditional colorimetric methods require the preparation of a separate "blank" vial. The extra step of preparing a blank vial can introduce error to the measurement based upon individual human techniques in preparing the blank. Also, since the traditional colorimetric technique involves the bleaching of a dye, the time for preparation and time a measurement is taken, can introduce variability in the sample reading. Additionally, because the techniques include bleaching of a dye, difficulty may arise because there may not be the same amount of starting colorimetric dye in both the blank and sample vial, thereby introducing error into the determination of the amount of analyte found in the sample. This error may result in a false positive or false negative result.

Additional limitations with current techniques include the incomplete mitigation of chlorine interference of an ozone measurement. For example, malonic acid, a salt of malonic acid, or the like do not mitigate chlorine interference. The use of arsenite presents environmental and storage problems. And reducing agents such as sulfate, bisulfite, or the like may react with ozone in addition to the free chlorine which leads to inaccurate ozone measurement.

Accordingly, an embodiment provides a system and method for measuring ozone in a sample. The sample may be drawn from a volume of liquid such as a holding tank, water source, food material source, beverage source, or the like. The sample may be free of other oxidants. In an embodiment, the method may detect ozone in concentrations in about the range of 0 to 2.1 parts per million (ppm). In an embodiment, the method may use a fluorometric method. The indicator may be an indigo-based indicator. The indigo-based indicator may be indigo carmine or Indigo-5,5'-disulfonate sodium salt. In an embodiment, the fluorescence may be correlated to the detection of ozone. In an embodiment, the fluorescence intensity or change in fluorescence may be correlated to ozone in a sample. A buffer such as phosphate buffer may be added. In an embodiment, the pH of a solution may be adjusted to activate the reporter or indicator molecule. The pH may be adjusted to about pH 7.0 or higher. Citrate salt may be added as an additive to mitigate hardness interference via chelation. In an embodiment, an ammonium salt may be added to the sample. The ammonium salt may be an inorganic ammonium salt like ammonium dihydrogen phosphate, diammonium hydrogen phosphate, ammonium chloride, ammonium acetate, ammonium citrate, ammonium tartrate etc. The ammonium salt may convert free chlorine to monochloramine to mitigate free chlorine interference in the sample. The use of ammonium salt does not impact ozone measurement.

The illustrated example embodiments will be best understood by reference to the figures. The following description is intended only by way of example, and simply illustrates certain example embodiments.

Referring to FIG. 1, an example system and method for detection of ozone in a sample is illustrated. In an embodiment, an indigo-based indicator may be prepared. The indigo-based indicator may be Indigo-5,5'-disulfonate sodium salt or indigo carmine. Indigo carmine indicator may be introduced to a sample containing ozone. In an embodiment, indigo carmine indicator in the presence of ozone may cause a change in fluorescence intensity of the indicator. The change of fluorescent intensity may be correlated to a concentration of ozone in the solution or sample.

Figure 2:
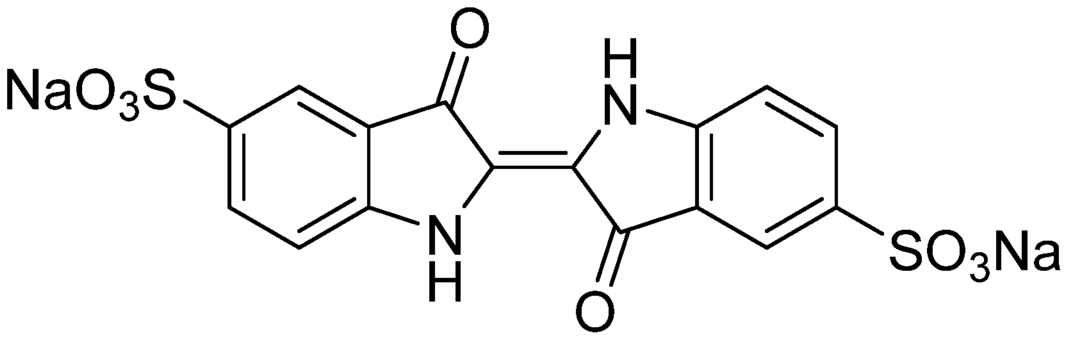
FIG. 2 illustrates a chemical formula of an indigo-based indicator.
Figure 3:
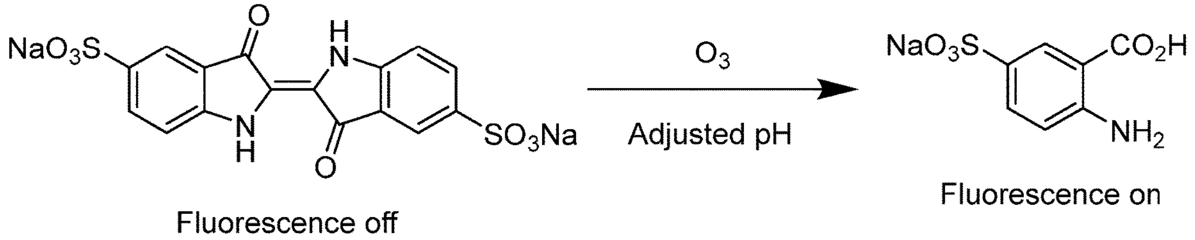
FIG. 3 illustrates a reaction scheme example of an indigo-based indicator for detection of ozone.

At 101, in an embodiment, an indigo-based may be prepared. The indigo-based indicator may be Indigo-5,5'-disulfonate sodium salt or indigo carmine (See FIG. 2). Referring to FIG. 3, an example reaction of indigo carmine indicator is illustrated. In an embodiment, indigo carmine indicator may detect ozone in the range of 0-2.1 mg/L. The range is exemplary, a range may be determined based upon the need to control ozone to a suitable level for water treatment for example.

At 102, in an embodiment, indigo carmine indicator may be introduced into a sample. The sample may contain ozone or an amount of ozone. The solution may be a sample which may include a sample from a natural body of water, a holding tank, a processing tank, a pipe, a water system, a volume of liquid for food preparation, or the like. The solution may be in a continuous flow, a standing volume of liquid, or any combination thereof. In one embodiment, the sample may be introduced to the indigo-based indicator, for example, a test chamber of the measurement device. Introduction of the sample into the measurement device may include placing or introducing the sample into a test chamber manually by a user or using a mechanical means, for example, gravity flow, a pump, pressure, fluid flow, or the like. For example, a water sample for ozone testing may be introduced to a measurement or test chamber using a pump. In an embodiment, valves or the like may control the influx and efflux of the solution into or out of the one or more chambers, if present.

Additionally, or alternatively, the measurement device may be present or introduced in a volume of the sample. The measurement device is then exposed to the volume of sample where it can perform measurements. The system may be a flow-through system in which a solution and/or reagents are automatically mixed and measured. Once the sample is in contact with the measurement system, the system may measure the ozone of the sample or a change in fluorescence of the sample, as discussed in further detail herein. In an embodiment, the measurement device may include one or more chambers in which the one or more method steps may be performed.

Figure 4:
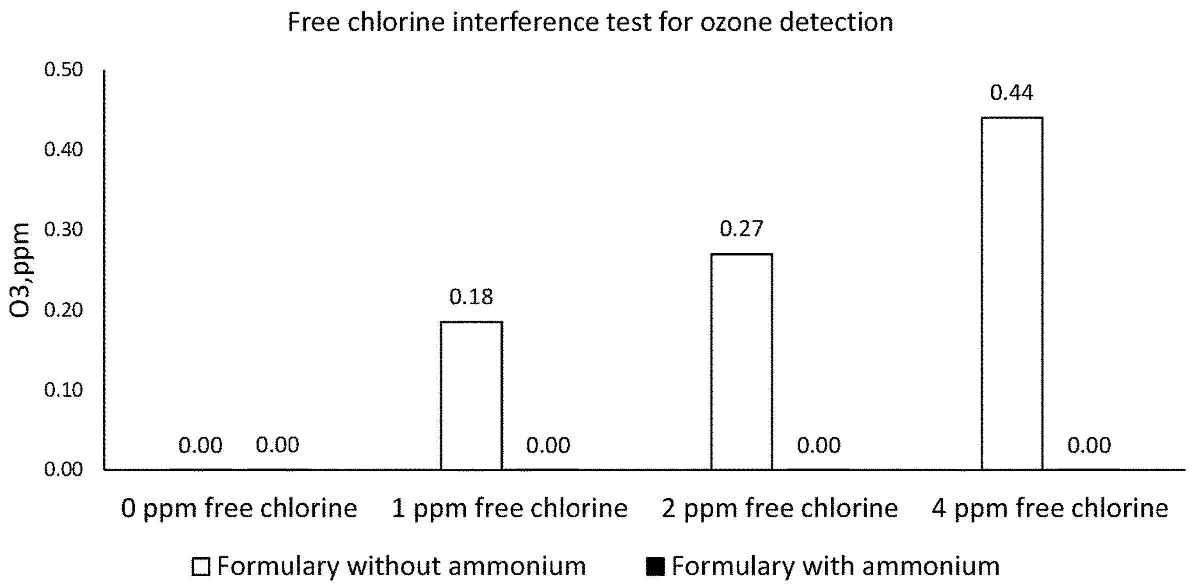
FIG. 4 illustrates example data of mitigation of free chlorine in a sample during ozone measurement.

At 103, in an embodiment, an ammonium salt may be added to the sample containing ozone. The indigo-based indicator either with or without ammonium salt may be referred to as a formulary to be added to a sample for measurement. The ammonium salt may convert free chlorine to monochloramine. Free chlorine may be an interferant to a measurement of ozone in the sample. Monochloramine does not interfere with the measurement of ozone in a sample. In other words, monochloramine does not interfere with the measurement of ozone using indigo carmine as an indicator (See FIG. 4). Sample data shows that the presence of ammonium salt in a range of about 0-4 ppm of free chlorine mitigates the interference of free chlorine to the measurement of ozone. In an embodiment, the ammonium salt may be in a concentration of about 2 mM. The ammonium salt may mitigate free chlorine up to approximately 120 ppm (parts-per-million). However, 10 ppm is a typical upper limit of free chlorine in a sample.

An embodiment of the reaction of ammonia with ozone and free chlorine are illustrated below:

$$HOCl + NH_3 \xrightarrow{k1} NH_2Cl + H_2O$$

$$4O_3 + NH_3 \xrightarrow{k2} H^+ + NO_3^- + H_2O + 4O_2$$

An embodiment of the reaction with indigo carmine with ozone and free chlorine are illustrated below:

$$HOCl + \text{Indigo carmine} \xrightarrow{k3} \text{Fluorescence reporter molecule}$$

$$O3 + \text{Indigo carmine} \xrightarrow{k4} \text{Fluorescence reporter molecule}$$

In an embodiment, the reaction scheme may mitigate free chlorine and detect ozone if: $k_1 >> k_3$ and $k_4 >> k_2$.

At 104, in an embodiment, the pH of the solution may be controlled, adjusted, or titrated. Additionally, or alternatively, ozone may be added to the solution. The ozone may be added to a sample using an ozone generator or may be present from another process. In an embodiment, indigo carmine indicator in the presence of ozone may "turn-on" the fluorescent properties of indigo carmine indicator. For example, the pH may be adjusted or titrated to around a pH in the range of about 7.0 or a higher pH value (more basic). Indigo carmine indicator concentration may be approximately 10-150 micromolar (μM). The indicator concentration may be adjusted based upon an ozone concentration in a sample. In an embodiment, a buffer may be added. The buffer may be a phosphate buffer. The phosphate buffer concentration may be about 75 mM. Citrate salt may be added as an additive to mitigate hardness interference via chelation. An approximate range of detection of ozone is between 0-2.1 mg/L or ppm (parts per million).

Figure 5:
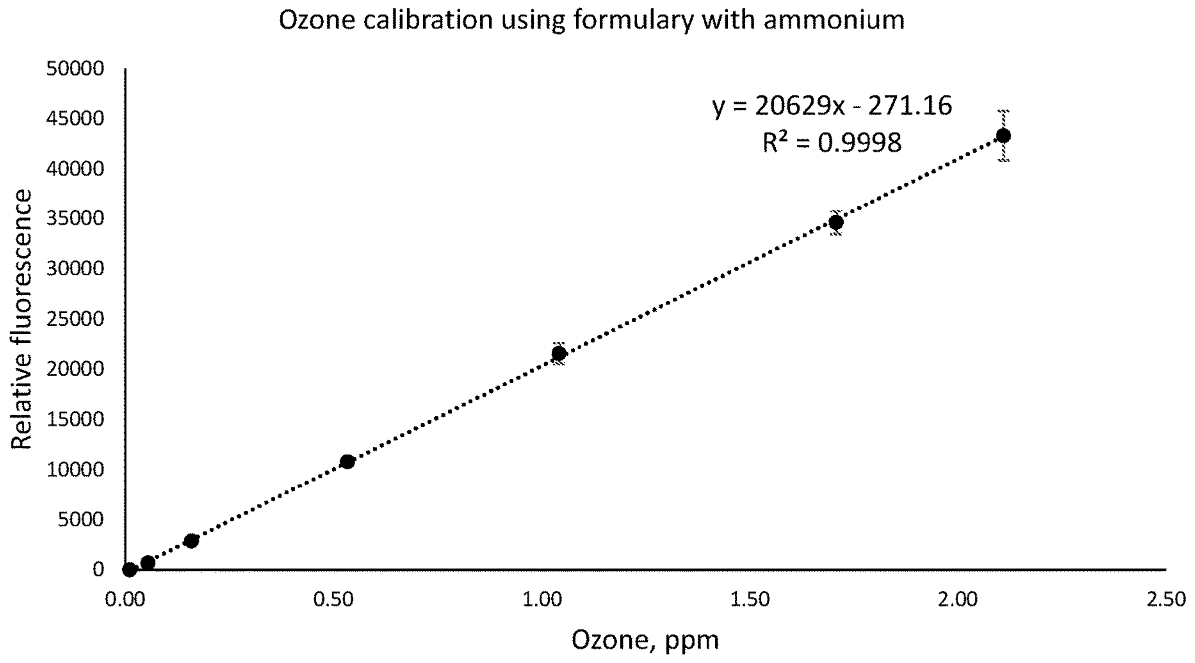
FIG. 5 illustrates an example ozone calibration curve using an indigo-based indicator in the presence of an ammonium salt.

At 105, in an embodiment, the system and method may determine if an ozone concentration may be determined. In an embodiment, the presence of ozone in a sample may cause an increase in fluorescence intensity of indigo-based indicator. Examples of this increase in fluorescence intensity and dose response curves for an indigo-based indicator may be illustrated in FIG. 5. An embodiment, of relative fluorescence units (RFU) is plotted over ozone concentration (ppm). For example, a change in fluorescence intensity may be measured over time, in real time, or the like. The change in fluorescence intensity may be a result of the reaction with the indigo-based indicator and an amount of ozone in the sample. In an embodiment, a blank vial may be compared to a reaction vial. The illustrated ozone concentration is from 0 to approximately 2.1 ppm. Experimental conditions may include generation of ozone with an ozone generator, at room temperature or chilling the sample to around 0-5 degrees Celsius, stirring the sample, pretreating the pipette tip by placing in the ozonated sample, and using a 10 cm cell to measure absorbance. These conditions are exemplary and may be altered based upon conditions. In an embodiment, indigo carmine indicator may be used at a final concentration 10-150 micromolar (μM).

The measured absorbance may be correlated to a concentration or amount of ozone in the sample or water. The correlation may be based off a UV-Vis measurement for ozone. This may be used as a reference measurement. The same aliquot may then be used in a 24±1 mm or 16 mm cell with buffer and an indicator. The sample may be diluted with deionized water depending on the ozone concentration. Measurements may be made using the Hach DR1300 FL (available from Hach Company, Loveland CO, USA) instrument to measure the RFU value or concentration versus the UV-Vis value. In an embodiment, an excitation wavelength may be between 320 and 385 nanometers (nm), preferably 365 nm. In an embodiment, an emission wavelength may be 420-470 nm, preferably 450 nm. In an embodiment, an excitation LED at 365 nm and PMT detector with 450 nm emission filter may be used to measure the fluorescence intensity. The fluorescence intensity is proportional to concentration of ozone. In an embodiment, a quartz cuvette may not be required. In an embodiment a glass or polymethyl methacrylate or acrylic cuvette may be used.

A phosphate buffer may be added. In an embodiment citrate may be added as an additive. The concentration of the citrate may be 15 mM. The citrate may prevent the formation of a metal phosphate by complexation.

Therefore, the fluorescence intensity, of a solution containing ozone may be correlated to the intensity of a change in the intensity in the sample or aqueous solution. Fluorescence curves may be generated for a range of concentrations, for different indigo-based indicators, for any different condition that may affect absorption or fluorescence values (e.g., temperature, sample content, turbidity, viscosity, measurement apparatus, aqueous sample chamber, etc.), or the like.

Alternatively, or additionally, ozone measurement may be at periodic intervals set by the user or preprogrammed frequencies in the device. Measurement by a device allows for real time data with very little human involvement in the measurement process. Cleaning of the fluorometric chamber may be required at an unspecified time interval. A programmed calibration curve may be entered into the device.

A chamber, vessel, cell, chamber, or the like may contain a sample, at least one indigo carmine indicator, and associated reagents such as buffers and/or additives. A device may contain one or more bottles of reagents which contain necessary reagents. The reagents contained in the one or more bottles may be pump fed or gravity fed. The flow of the reagents may be metered to ensure proper volume delivery to the measurement cell. The sample may be fed through a pressured inlet, a vessel, or the like. The sample may be introduced into the measurement chamber by a pump or gravity fed. The sampling device may be in series or parallel to an aqueous flow. The device may have a system to ensure proper mixing of the aqueous sample, indigo carmine indicator, and related reagents.

The fluorescent intensity or ozone concentration may be an output upon a device in the form of a display, printing, storage, audio, haptic feedback, or the like. Alternatively, or additionally, the output may be sent to another device through wired, wireless, fiber optic, Bluetooth®, near field communication, or the like. An embodiment may use an alarm to warn of a measurement or concentration outside acceptable levels. An embodiment may use a system to shut down water output or shunt water from sources with unacceptable levels of an analyte. For example, an analyte measuring device may use a relay coupled to an electrically actuated valve, or the like.

At 107, in an embodiment, if a concentration of ozone cannot be determined, the system may continue to measure ozone, changes in fluorescence intensity and/or fluorescence intensity. Additionally, or alternatively, the system may output an alarm, log an event, or the like.

If a concentration of ozone can be determined, the system may provide a measurement of ozone concentration at 106. The system may connect to a communication network. The system may alert a user or a network. This alert may occur whether an ozone measurement is determined or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if an ozone concentration reaches a threshold. Alarms or logs may be analyzed in real-time, stored for later use, or any combination thereof.

The various embodiments described herein thus represent a technical improvement to conventional ozone measurement techniques. Using the techniques as described herein, an embodiment may use an indigo carmine indicator to measure ozone in solution. This is in contrast to methodology with limitations mentioned above. Such techniques provide a faster and more accurate method for measuring ozone in an aqueous or liquid solution. The various embodiments described herein thus represent a technical improvement to precise ozone measurement in a sample. Using the techniques as described herein, an embodiment may use a method and device to measure ozone concentration. This is in contrast to conventional methods with limitations mentioned above.

Figure 6:
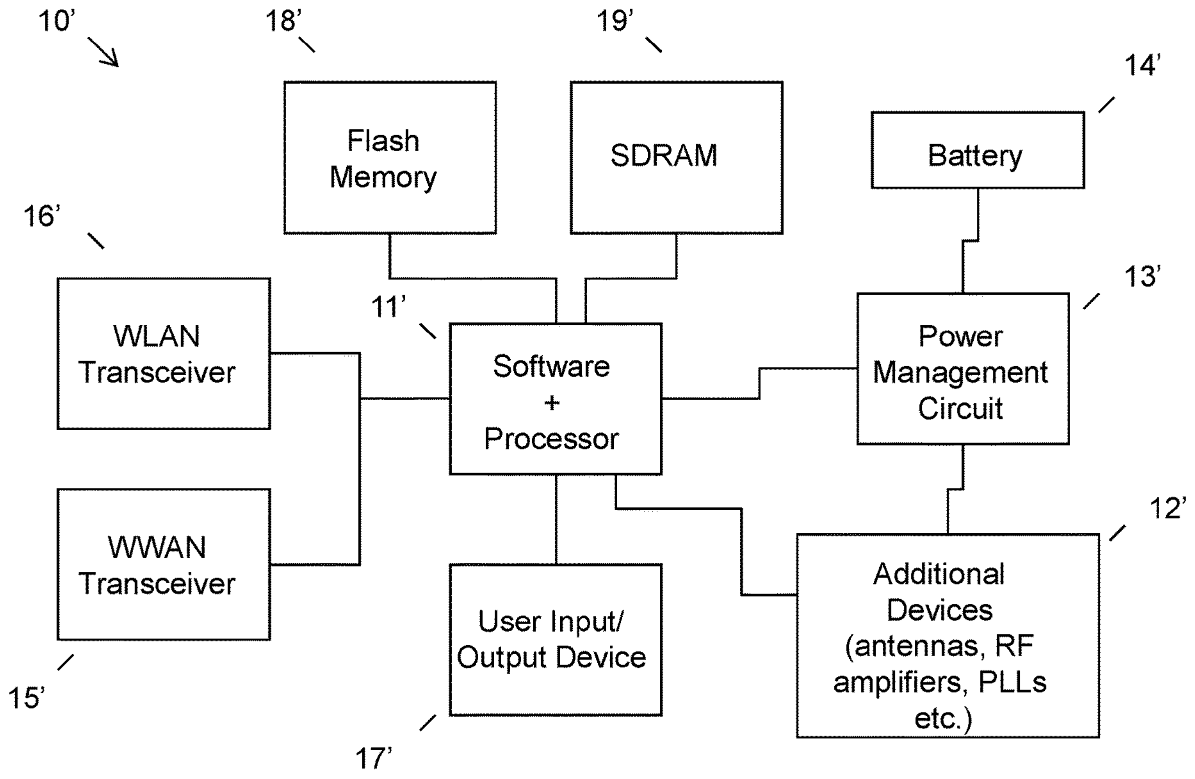
FIG. 6 illustrates an example of computer circuitry.

While various other circuits, circuitry or components may be utilized in information handling devices, with regard to an instrument for ozone measurement in according to any one of the various embodiments described herein, an example is illustrated in FIG. 6. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform ozone measurement of a sample.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a handheld measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring ozone in a sample, comprising:
measuring a first intensity of fluorescence of a sample that contains an amount of ozone;
introducing an indigo-based indicator and an ammonium salt at about 2.0 millimolar to the sample;
measuring a second intensity of fluorescence of the sample containing ozone after the introduction of the indigo-based indicator and the ammonium salt;
measuring a change in intensity of the fluorescence between the first and second fluorescence intensities; and
measuring the amount of ozone in the sample based upon the measured change in intensity of the fluorescence.

2. The method of claim 1, wherein the indigo-based indicator is indigo-5,5'-disulfonate sodium salt.

3. The method of claim 1, further comprising titrating the sample to a pH of about 7.0.

4. The method of claim 1, further comprising titrating the sample to a pH of greater than 7.0.

5. The method of claim 1, further comprising adding a phosphate buffer to the sample with the indigo-based indicator.

6. The method of claim 1, wherein the amount of ozone is in a range of 0-2.1 mg/L.

7. The method of claim 1, wherein the change in fluorescence intensity is correlated to a concentration of the ozone in the sample.

8. The method of claim 1, wherein the measuring of the change in intensity of the fluorescence uses an excitation wavelength between 320 and 370 nm and an emission wavelength between 420 and 470 nm.

9. The method of claim 1, wherein measuring of the change in intensity of the fluorescence occurs in a cuvette made of a material selected from the group consisting of: glass, polymethyl methacrylate, and acrylic.

10. The method of claim 1, wherein the sample comprises water from a beverage material system.

11. A method for measuring ozone in a sample, comprising:
measuring a first intensity of fluorescence of a sample that contains an amount of ozone;
introducing an indigo-based indicator and an ammonium salt at about 2.0 millimolar to the sample;
adjusting the sample to a pH value;
measuring a second intensity of fluorescence of the sample containing ozone after the introduction of the indigo-based indicator and the ammonium salt;
measuring a change in intensity of the fluorescence between the first and second fluorescence intensities; and
measuring the amount of ozone in the sample based upon the measured change in intensity of the fluorescence.

12. The method of claim 11, wherein the indigo-based indicator is indigo-5,5'-disulfonate sodium salt.

13. The method of claim 11, wherein the pH value comprises a pH of about 7.0.

14. The method of claim 11, wherein the pH value comprises a pH of greater than 7.0.

15. The method of claim 11, further comprising adding a phosphate buffer to the sample with the indigo-based indicator.

16. The method of claim 11, wherein the amount of ozone is in a range of 0-2.1 mg/L.

17. The method of claim 11, wherein the change in fluorescence intensity is correlated to a concentration of the ozone in the sample.

18. The method of claim 11, wherein the measuring of the change in intensity of the fluorescence uses an excitation wavelength between 320 and 370 nm and an emission wavelength between 420 and 470 nm.

19. The method of claim 11, wherein measuring of the change in intensity of the fluorescence occurs in a cuvette made of a material selected from the group consisting of glass, polymethyl methacrylate, and acrylic.

20. A measurement device which measures ozone in a sample, comprising:
an indigo-based indicator;
at least one measurement chamber;
a processor; and
a memory storing instructions executable by the processor to:
measure a first intensity of fluorescence of a sample that contains an amount of ozone;
introduce the indigo-based indicator and an ammonium salt at about 2.0 millimolar to the sample;
measure a second intensity of fluorescence of the sample containing ozone after the introduction of the indigo-based indicator and the ammonium salt;
measure a change in intensity of the fluorescence between the first and second fluorescence intensities; and
measure the amount of ozone in the sample based upon the measured change in intensity of the fluorescence.

* * * * *